United States Patent [19]

Faccioli et al.

[11] Patent Number: 6,015,413
[45] Date of Patent: Jan. 18, 2000

[54] DEVICE FOR THE EXTRACTION OF SCREW-THREADED WIRES PARTICULARLY FOR ORTHOPAEDIC SURGICAL OPERATIONS

[75] Inventors: Giovanni Faccioli, Monzambano; Daniele Venturini, Povegliano Veronese, both of Italy; Dietmar Pennig, Köln, Germany

[73] Assignee: Orthofix S.r.l., Bussolengo, Italy

[21] Appl. No.: 08/981,513

[22] PCT Filed: Feb. 29, 1996

[86] PCT No.: PCT/IB96/00155

§ 371 Date: Dec. 22, 1997

§ 102(e) Date: Dec. 22, 1997

[87] PCT Pub. No.: WO97/00648

PCT Pub. Date: Jan. 9, 1997

[30] Foreign Application Priority Data

Jun. 20, 1995 [IT] Italy ................................. VR95A0055

[51] Int. Cl.[7] ............................. A61B 17/58; A61B 17/60
[52] U.S. Cl. ............................................................. 606/104
[58] Field of Search ............................... 606/53, 100, 104, 606/103

[56] References Cited

U.S. PATENT DOCUMENTS 5,476,467  12/1995  Benoist .................................... 606/100
5,531,751  7/1996  Schultheiss et al. ..................... 606/100

FOREIGN PATENT DOCUMENTS

P4309707  3/1993  Germany .
4406374C2  2/1994  Germany ........................ A61B 17/58

*Primary Examiner*—Michael Buiz
*Assistant Examiner*—Vy Q. Bui
*Attorney, Agent, or Firm*—Hopgood, Calimafde, Kalil & Judlowe

[57] ABSTRACT

A device for the extraction of screwthreaded sires for osteosynthesis, characterized in that it comprises: at least two lever pieces (20, 21) hinged together and having at one longitudinal end (20a, 21a) seats (22, 23) for grasping the end of a wire (19) which it is required to extract, and clamp means acting on the ohter end of said lever pieces (20, 21) to promote their opening in such a way as to generate a couple of gripping forces on the end of the wire (19). Said clamp means are of screw type and preferably consist of a threaded pin (24) fitted with a knob (24a) and screwed into a tapped piece (25) integral with the end (21b) of one of said lever pieces (21). The end (24b) of the threaded pin nearest the pivot is of a generally frustoconical shape to interact with an inclined plane surface (26) formed in the end (20b) of the other lever piece (20) in such a way as to force it outwards when said pin (24) is screwed in. The thread on said pin (24) and on the tapped piece (25) is opposite to that of the thread of the wires (19).

12 Claims, 5 Drawing Sheets

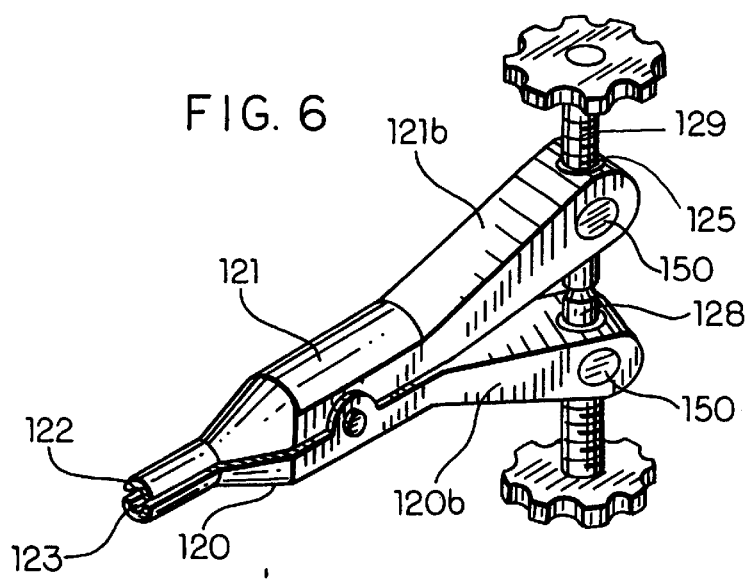
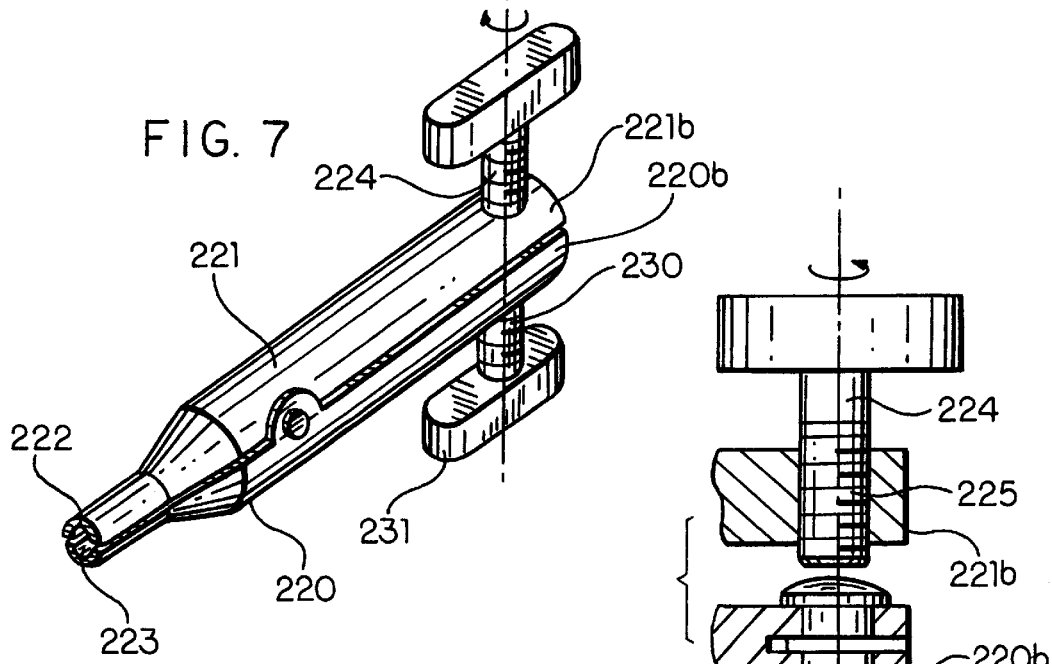
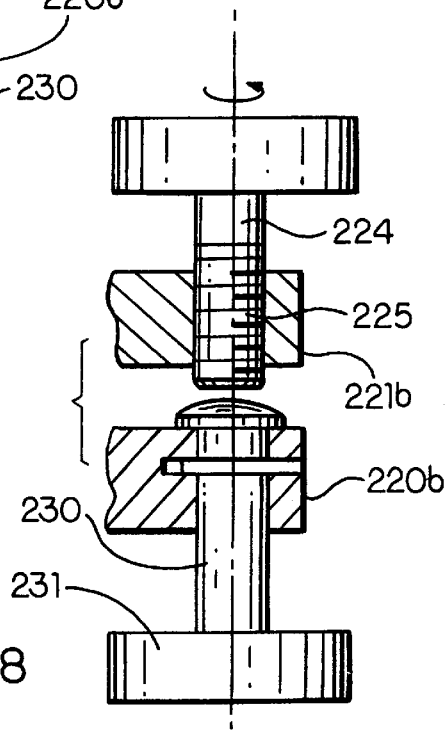

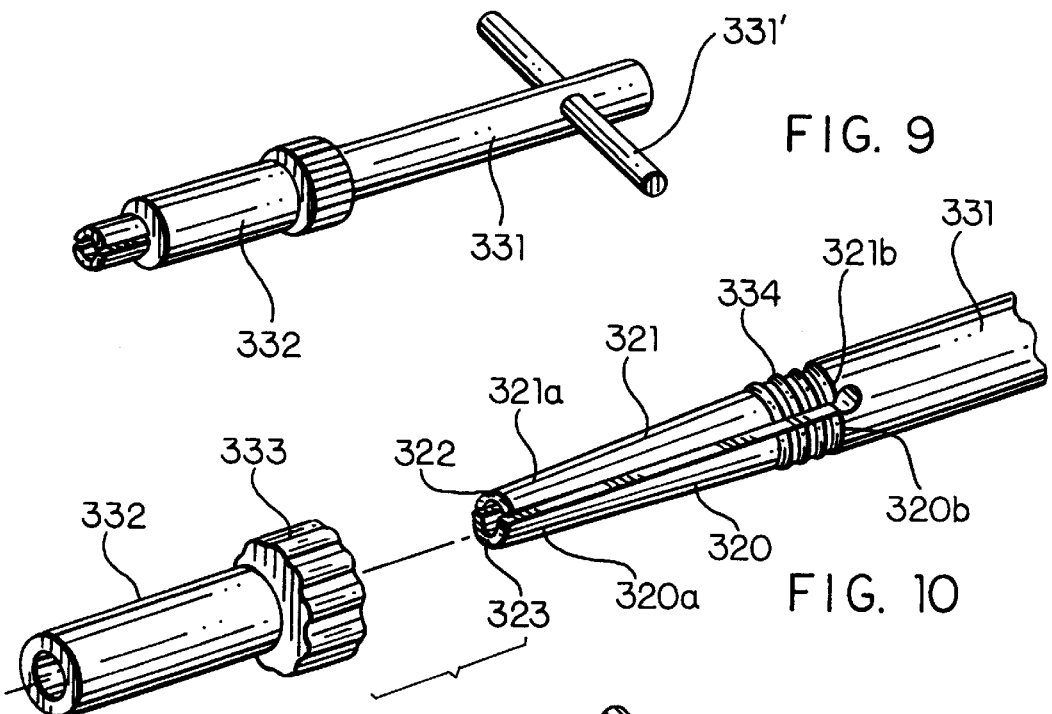
FIG. 9
FIG. 10
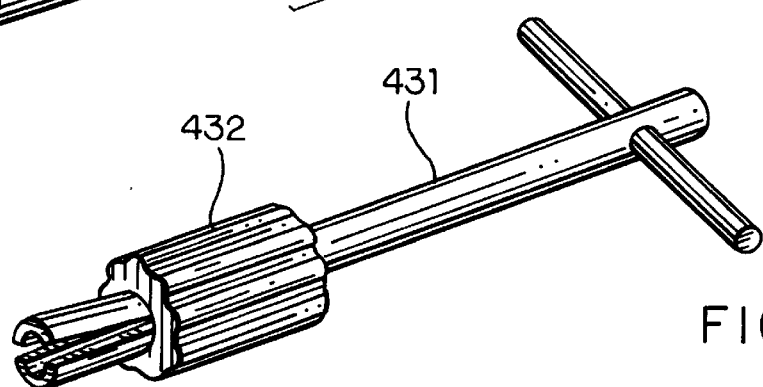
FIG. 11
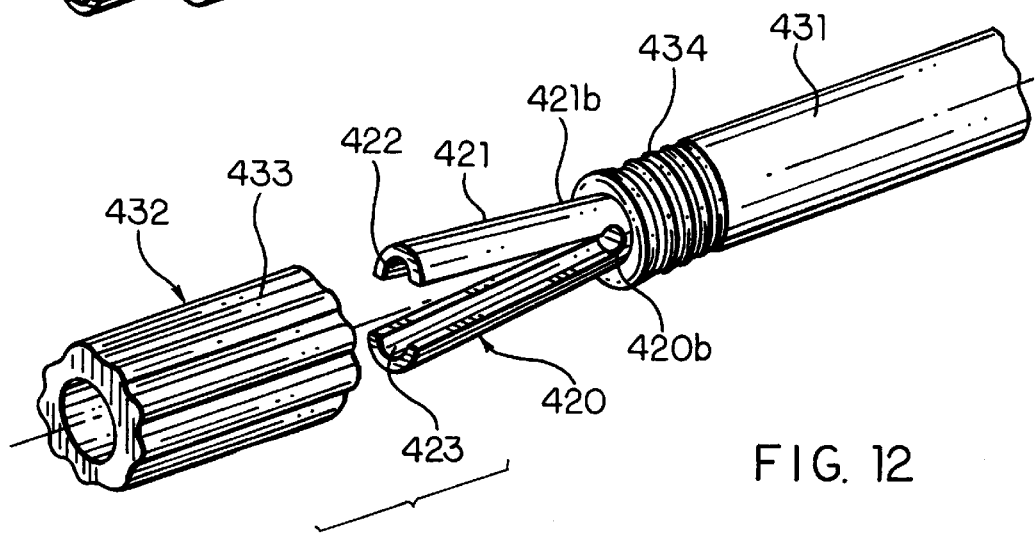
FIG. 12

DEVICE FOR THE EXTRACTION OF SCREW-THREADED WIRES PARTICULARLY FOR ORTHOPAEDIC SURGICAL OPERATIONS

The present invention relates to a device for the extraction of screwthreaded wires for osteosynthesis at the end of treatment.

As is known from German Patent Application No. P4309707 published in the file of DE-44,06,374-C, screwthreaded wires are an improvement on the Kirschner's wires used in orthopaedic surgery for compacting bone fragments onto the main bone or in the reconstruction of small fractured bones. Unlike Kirschener's wires, screwthreaded wires are not completely smooth: instead, the end that is to be inserted into the bone is threaded, and the diameter of the thread is less than that of the remaining cylindrical shank of the wire. There is thus a shoulder at the point where the screwthreaded part ends and the smooth part begins. This shoulder serves to exert a compressive action on the bone fragment towards the part of the bone from which said fragment has become detached, when the screwthreaded wire is screwed in.

Depending on the characteristics and dimensions of the bone fragment and of the bone from which said fragment has become detached, screwthreaded wires of different diameters and with different thread diameters are used, as for example 1.5-mm, 2.0-mm, or 3.0-mm diameter wires with thread diameters of 1.2 mm, 1.6 mm or 2.2 mm respectively, and with different lengths of the threaded part.

When the treatment is finished, that is to say when the bone fragment has become firmly fixed to the bone from which it was detached, the screwthreaded wire or wires must be removed.

A known method for the extraction of screwthreaded wires for osteosynthesis involves using ordinary forceps consisting of two levers giving mechanical advantage which are held by their longer arms and enable a gripping couple to be produced in the two jaws provided on the shorter arms.

During the operation of extracting a wire with forceps the following problem can arise.

Since the operator (the orthopaedic surgeon) is wearing elastic gloves his grip may relax as a result of slight slippages between his hand and the tool. This produces a relaxing of the effort applied to the levers and consequently a reduction in the gripping forces, as a result of which the jaws may slip on the end of the wire is to be extracted.

Also known is a wire-extracting device consisting of a spanner in which the opposite end from that on which the grip is formed contains a cylindrical seat in which the cylindrical end of the wire to be extracted is accommodated. In the side wall of said cylindrical cavity is a set screw whose axis is perpendicular to the axis of said cylindrical cavity. This screw can be driven from the outside by a hexagon socket wrench in order to clamp the end of the wire to be extracted.

The problem with the known extractor device is that it cannot be used for removing a wire whose end is completely below the skin of the patient from whom the wire is to be extracted, The cause in order to clamp the cylindrical end of the wire to be extracted in this instrument, it is necessary to turn said set screw, and since the latter must grip the lateral surface of said end, it would be necessary to work underneath the external surface of the skin, a position which is virtually inaccessible.

During the operations of removing the wire, the known extractor devices must be turned together with the wire itself, and in cases in which the end of the wire is deep below the external surface of the skin there could be accidental impact of the instrument on the soft tissues surrounding the end of the wire in question.

U.S. Pat. No. 4,438,769 discloses a device for holding, driving and withdrawing a medical staple, comprising a staple retaining member having spaced and opposed portions normally and inherently urged away from each other and being adapted to receive and retain a medical staple therebetween, the spaced and opposed portions having force application surfaces to which force may be applied to overcome the normal and inherent urging away force to releasably retain a medical staple therebetween; and a force applying and force reduction member cooperatively associated with said integrally constructed staple retaining member for selective application or removal of discrete forces upon said force application surfaces.

FR-A-1,322,212 discloses an apparatus intended to withdraw pins used in bone surgery, in particular pins in the form of threaded rods, comprising a rod, one end of which is screwed into a tube, the other end of the rod having a hole bored along its axis, the rod and the tube each being provided with handles, the diameter of the hole being variable in accordance with the tightening force which a conical end of the tube exerts on a conical wall of the hole when the rod is screwed into the tube using the handles.

The closest prior art to the present invention is represented by document AUB-75,239/87 which discloses in FIGS. 3–10c and the description page 4, second paragraph: a device suitable for the extraction of screwthreaded wires suitable for osteosynthesis which comprises: at least two lever pieces hinged together and having at one end longitudinal end seats or jaws suitable for grasping the end of a wire which it is required to extract, and clamp means acting on the other ends of said lever pieces to promote their opening or closing in such a way as to generate at least one gripping couple on the end of the wire.

The precharacterizing portion of claim 1 is based upon this prior art.

It is the chief object of the present invention to provide orthopaedic surgeons with a device for the extraction of screwthreaded wires for osteosynthesis which can be held firmly and which, if the operator's grip should relax, does not relax its grip on the end of the wire.

The present invention also aims to provide a device for the extraction of a wire that would also be able to extract wires whose ends are well below the external surface of the skin, requiring only a small incision into the skin to get at the end of the wire and also avoiding, or reducing to a minimum, the impact between the device and the soft parts of the surrounding tissues.

In accordance with the present invention there is provided a device for extracting screwthreaded wires for osteosynthesis, comprising at least two lever pieces hinged together and having at one longitudinal end thereof seats or jaws for grasping the end of a wire which is required to be extracted, and manually operable clamp means acting on the other end of said lever pieces to promote opening or closing thereof to thereby generate at least one gripping couple on the end of the wire, and characterized in that said clamp means are provided with means for preventing relaxation of the grip on the end of the wire to be extracted, and said seats or jaws are provided with means for gripping the end of the wire, said relaxation-preventing means including at least a threaded pin mounted at one end of one of the lever pieces for selectively locking the end of the other lever piece, said gripping means having semicylindrical cavities whose diameter is approximately equal to the diameter of the wire to be extracted and whose longitudinal axis is coaxial with the longitudinal axis of the device, and having a first cylindrical end part whose diameter is slightly greater than the diameter of the wire to be extracted and a second, generally frusto-conical part joining said first part and a generally cylindrical central part of the two lever pieces thereby to enable the wire to be gripped beneath the surface of the skin.

The threaded pin is preferably fitted with a knob and screwed onto a tapped piece integral with the end of one of said lever pieces. The end of the screwthreaded pin nearest the pivot is preferably of a generally frustoconical shape to interact with an inclined plane surface formed at the end of the other lever piece in such a way as to force it outwards when said pin is screwed in. The hand of the thread on said pin and on the tapped piece is opposite to that of the thread on the wires.

A first advantage offered by the proposed invention consists in the fact that the device has a mechanism for locking the end of the wire which it is required to extract, so that the operator can briefly relax his grip on said device without having the extraction device relax its own grip on the end of the wire as a result. Furthermore, the jaws of this device increase their clamping force as the device turns with and unscrews the screwthreaded wire by virtue of the fact that the hand of the thread of the clamping mechanism is opposite to that of the wire to be extracted.

A second advantage lies in the fact that the proposed device makes it possible also to remove screwthreaded wires whose ends are buried in the soft tissues and thus not projecting above the skin. This is due to the fact that the seats or jaws are provided with means for gripping the end of the wire below the extended surface of the skin.

Other advantages will become clear in the following detailed description which explains a number of possible examples of embodiments of the present invention—no limitation being implied, with reference to the accompanying drawings, in which:

FIG. 6 is a perspective view of a second embodiment of the device according to the present invention;

FIG. 7 is a perspective view of a third embodiment of the device according to the present invention; and FIG. 8 is a sectional view of a detail of the device shown in FIG. 7;

FIG. 9 is a perspective view of a fourth embodiment of the device according to the present invention;

FIG. 10 is an exploded partial perspective view of the device show in FIG. 9;

FIG. 11 is a perspective view of a fifth embodiment of a device according to the present invention;

FIG. 12 is an exploded partial perspective view of the device shown in FIG. 11;

Figure 1:
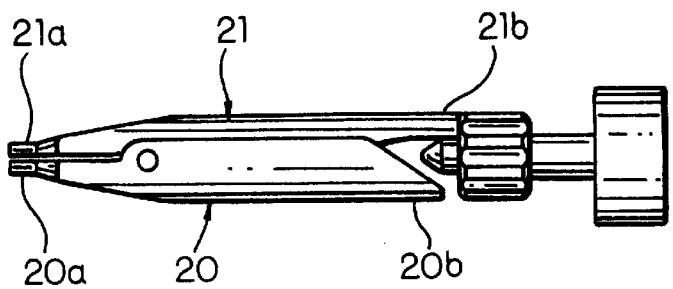
FIG. 1 is a front view of a device for the extraction of screwthreaded wires according to the present invention.

With reference to FIGS. 1 to 5, it will be seen that in a first embodiment the device according to the invention comprises: two lever pieces 20 and 21 hinged together and having at respective longitudinal ends 20a and 21a seats 22 and 23 for grasping the end of a wire 19 which it is required to extract, and clamp means 24–25 acting on the other end 20b and 21b of said lever pieces 20 and 21 to promote their opening or closing in such a way as to generate at least one gripping couple on the end of the wire 19.

As illustrated in FIG. 1, the clamp means 24–25 are of a screw type and consist of a screwthreaded pin 24 screwed into a tapped piece 25 integral with the end 21b of the lever piece 21. The axis of forward movement of said clamp means 24–25 is generally parallel with the second lever piece 21. The end 24b of the screwthreaded pin 24 nearest the pivot of said two lever pieces 20 and 21 is of a generally frustoconical shape to interact with an inclined plane surface 26 formed at the end 20b of the first lever piece 20, in such a way as to force it outwards when said pin is screwed in.

The hand of the threads on the pin 24 and on the tapped piece 25 is opposite to that of the thread on the wires. In this way, as the operator continues to screw the pin 24 into the tapped piece 25, once the ends 20a and 21a of said lever pieces have closed on the end of the wire to be extracted, the rotation of the device is such as to unscrew the wire and thus extract it.

Figure 2:
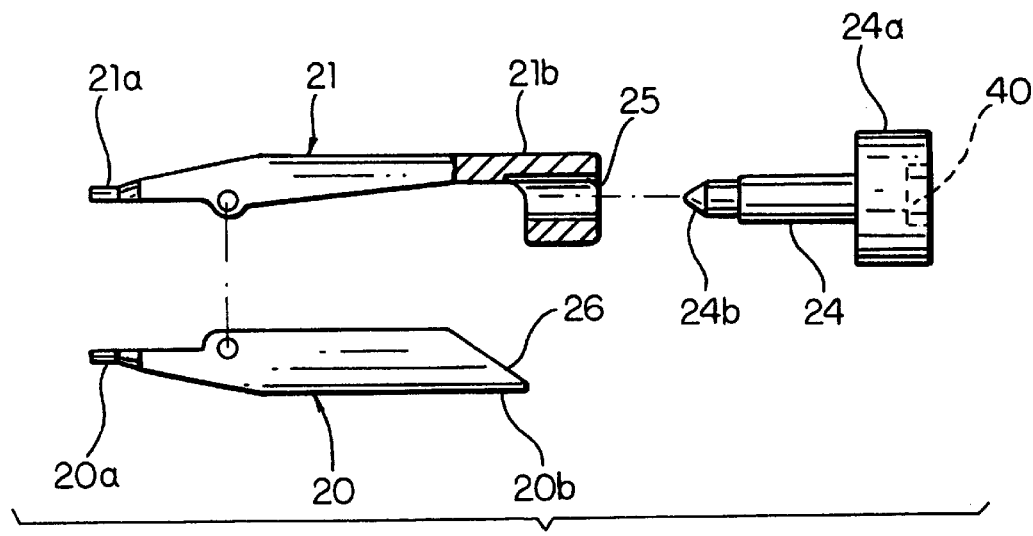
FIG. 2 is an exploded view of the device of the previous figure.

The pin 24, illustrated in detail in FIG. 2, is provided, at the end opposite to that 24b of generally frustoconical shape, with a knob having a generally polygonal cavity 40 whose longitudinal axis is coaxial with the axis of said pin, which cavity is suitable for the insertion of a polygonal socket wrench (key), not illustrated in the drawings, which facilitates the operations of screwing the pin 24 and thus unscrewing the screwthreaded wire which it is required to extract.

Figure 3:
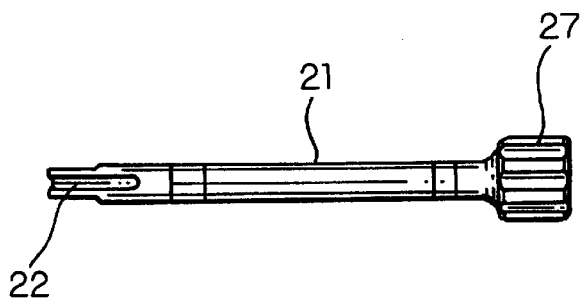
FIG. 3 is a view from below of a first lever piece of the device shown in FIG. 1.

As can be seen in FIGS. 1 and 3, the tapped piece 25 consists of a collar with a grooved outer surface 27 suitable for use as a knob to provide a better purchase during the extraction, by unscrewing, of the wire.

Figure 4:
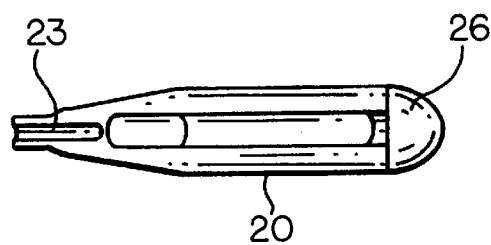
FIG. 4 is a view from above of a second lever piece of the device shown in FIG. 1.
Figure 5:
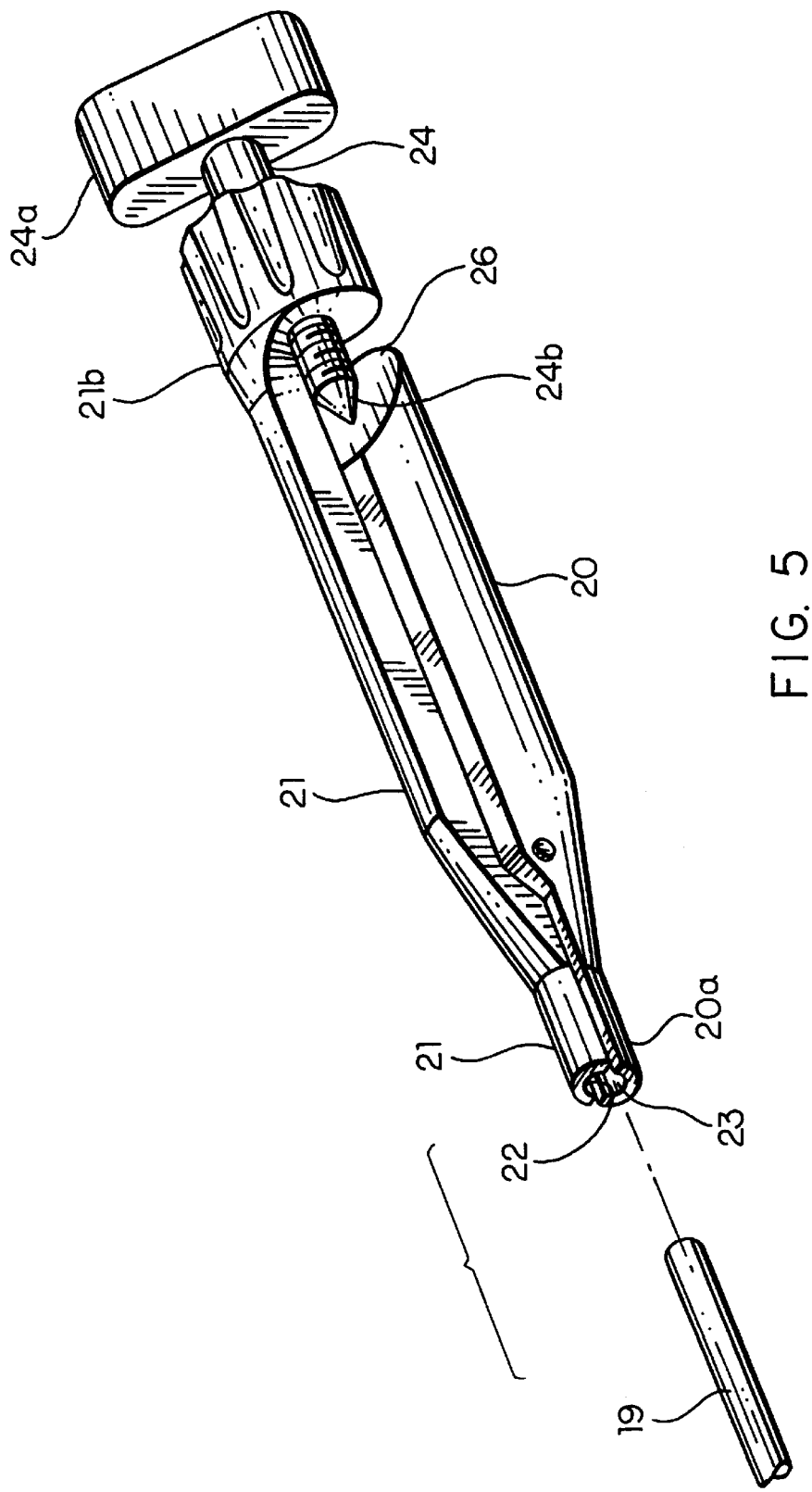
FIG. 5 is a perspective view of the device shown in FIG. 1.

As illustrated in FIGS. 3 and 4, the opposing surfaces of the ends of the two lever pieces are formed into seats 22 and 23 for grasping the end of a wire which it is required to extract. Said seats consist of semicylindrical cavities whose diameter is approximately equal to the diameter of the wire to be extracted and whose longitudinal axis is coaxial with the longitudinal axis of said device.

The longitudinal ends of the two lever pieces furthest from that to which the screw-tape clams means are fitted, and containing said seats 22 and 23, are each formed by a first, cylindrical end part whose diameter is slightly greater than the diameter of the wire to be extracted and by a second, generally frustoconical part joining said first part and the generally cylindrical central part of the pair of lever pieces. Said end of the extractor device has been designed thus designed or conceived in order that, when the device is used to extract a wire whose end is buried in soft tissues, turning the device causes the least possible damage to those tissues.

Illustrated in FIG. 6 is a second embodiment of the device for the extraction of screwthreaded wires, according to the present invention, in which, in contrast to the previous embodiment, the axis of forward movement of the screw-type clamp means is generally perpendicular to the longitudinal axis of said device. In this embodiment the pin 124 comprises two threaded portions 128 and 129 engaged in corresponding threads in tapped pieces 125 formed in the ends 120b, 121b of said lever pieces 120 and 121. The threads of the threaded portions 128 and 129 (and accordingly the threads of the topped pieces 125) are of mutually opposite hand so that turning said pin in one sense causes said lever pieces to open and turning the pin in the opposite sense causes said lever pieces to close.

Rather than be formed directly in the ends 120*b*, 121*b* of said lever pieces 120 and 121, the tapped pieces 125 can be formed by inserting two cylindrical pieces 150, in which two tapped cavities of the same dimensions as the thread of said portions 128 and 129 are made, in corresponding cavities formed in said ends 120*b*, 121*b* of the lever pieces. This embodiment illustrated in FIG. 6 makes it possible to give the two lever pieces 120 and 121 the right surface finishes appropriate to the type of use of the insturment separately from the threaded peices.

FIG. 7 illustrates a third embodiment of the device for the extraction of screwthreaded wires according to the present invention, in which the axis of forward movement of the screw-type clamp means is again generally perpendicular to the longitudinal axis of said device. However, as can be seen more clearly in FIG. 8, said screw-type clamp means consist of a pair of pins 224 and 230, the first of which screws into the end 221*b* of the second lever piece of the extractor device, while the second is integral with the end 220*b* of the first lever piece and, in combination with the pin 224, provides a means of holding the device.

FIG. 9 illustrates a fourth embodiment of the device for the extraction of screwthreaded wires according to the present invention, in which the axis of forward movement of the screw-type clamp means is generally parallel with one of the two lever pieces 320 and 321.

The lever pieces 320 and 321 are so formed that together they offer a generally frustoconical shape converging towards their first ends 320*a*, 321*a*, and are elastically hinged at their second ends 320*b*, 321*b* to form a body 331 to which is attached a rod 331' for screwing/unscrewing the wire to be extracted, when the jaws of the device have been clamped tightly on the end of the wire to be extracted. The gripping couple on the end of the illustrated in detail in FIG. 10, that is generally frustoconical and hollow, about a threaded portion 334 of said two lever pieces which is located near the pivot of these pieces.

The ring nut 332 also includes a knob 333, knurled for easy purchase, for bending the two lever pieces so that their ends 320*a*, 321*a* containing the seats 322 and 323 for gripping the end of a wire to be extracted, squeeze the end of this wire.

FIGS. 11 and 12 illustrate a fifth embodiment of the present invention that differs from that described immediately above in that the two lever pieces 420 and 421 are formed in such a way that together they present a generally frustoconical shape converging towards their second ends 420*b*, 421*b* near the pivot.

Figure 13:
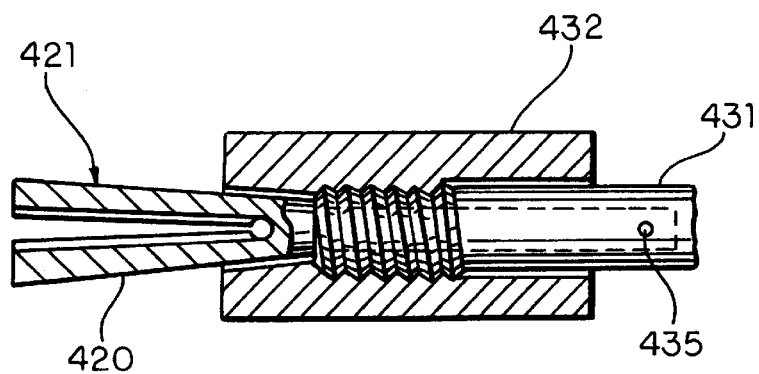
FIG. 13 is a partial sectional view of the device shown in FIG. 11.

FIG. 13 is a longitudinal section through the device depicted in FIGS. 11 and 12 with the locking ringnut 432 fully screwed onto the threaded portion 434 of the body 431. In this position the device is ready to accommodate the end of the wire to be extracted in its seats 422 and 423 formed at the ends 420*a* and 421*a* of the two lever pieces 420 and 421. The couple of forces required to grip said wire end is produced simply by partly unscrewing the ringnut 432 so that it moves towards the ends 420*a* and 421*a* of said two lever pieces.

It is clear in FIG. 13 that the two lever pieces 420 and 421 can be made as a single part which is then fixed to said body 431 by means of a pin 435 or any other suitable means for fixing the two parts together.

The two lever pieces and the body can obviously equally well be made as a single part, as in the embodiment illustrated in FIG. 10. Likewise the embodiment illustrated in FIG. 10 can obviously be made with the two lever pieces 320 and 321 in a single part which is then fixed to the body 331 by means of a pin or any other suitable means for fixing the two parts together.

This embodiment has the advantage that the locking ringnut 432 is unable to unscrew itself on its own from the pair of lever pieces 420 and 421.

This is because in order to remove the locking ringnut 432 completely from the pair of lever pieces 420 and 421 it is necessary to apply a force parallel to the longitudinal axis of the extractor device. When the ringnut 432 has been unscrewed from the threaded portion 434 and is slid in the longitudinal direction, its internal surface comes into contact with the external surface of the two lever pieces 420 and 421 which, because they taper down towards their pivot, prevent the ringnut from working itself loose. Only if the two lever pieces are bent elastically and their ends 420*a* and 421*a* brought together can the ringnut slide longitudinally far enough to come completely off the device. This prevents the ringnut from accidentally working itself loose during the earlier operations of gripping the end of the wire which it is required to extract.

Figure 14:
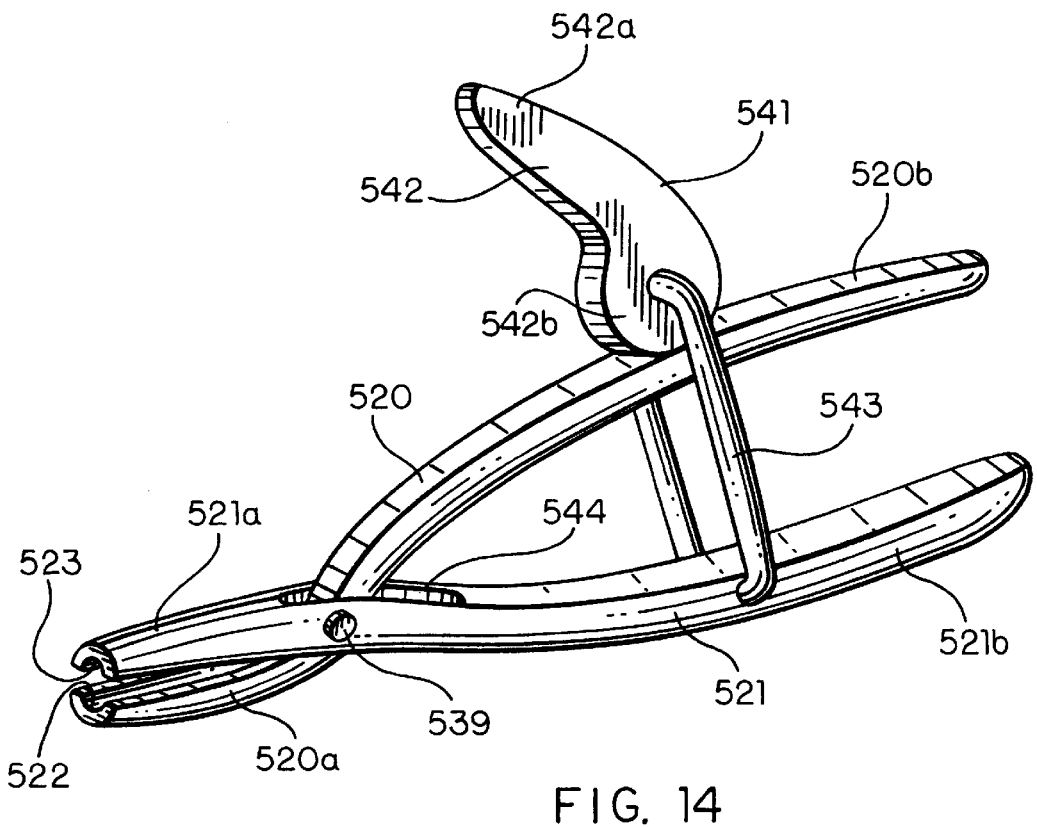
FIG. 14 is a perspective view of a sixth embodiment of the device according to the present invention.

Lastly, FIG. 14 illustrates a sixth embodiment of the invention, in which the two lever pieces 520 and 521 are hinged together by a pin 539 to form forceps. A return spring 544 is inserted close to said pin to enable the extractor device to remain in the open position in the absence of external action, that is to say with the ends 520*a* and 521*a*, containing the seats 522 and 523 for gripping the end of a wire to be extracted, apart.

The clamp means consist of a lever device 541 comprising a camming rod 542 and a ring 543 for the pivoting of said rod 542. Said ring is also anchored, at the opposite side from that secured to said rod 542, to one end 521*b* of one lever piece 521 of the extractor device.

The ring 543 could obviously equally well be anchored to the lever piece 520, in which case the rod 542 would act on the end 521*b* of the lever piece 521.

The lever device 541 is so located as to enable the operator who is holding the extractor device to act on the end 542*a* of said lever to force this end 542*a* towards the piece 520, thus increasing the gripping couple on the end of the wire which it is required to extract, for by so doing the device 541 is made to exert a force on the lever piece 520 at the point of contact of the suitably shaped rod 542 with the end 520*b* of the lever piece 520, so tending to close or urging together the two ends 520*b* and 521*b* of the two lever pieces. The closer the end 542*a* of the rod 542 comes to the piece 520, the more the two lever pieces 520 and 521 of the extractor device are forced to squeeze the jaws 520*a* and 521*a* of said device, and thus produce the couple of forces necessary to grip the end of the wire to be extracted.

We claim:

1. Device for extracting screwthreaded wires for osteosynthesis, comprising at least two lever pieces (20–21, 120–121, 220–221) hinged together and having at one longitudinal end thereof (20*a*–21*a*, 120*a*–121*a*, 220*a*–221*a*) seats or jaws (22–23, 122–123, 222–223) for grasping the end of a wire (19) which is required to be extracted, and manually operable clamp means acting on the other end (20*b*–21*b*, 120*b*–121*b*, 220*b*–221*b*) of said lever pieces to promote opening or closing thereof to thereby generate at least one gripping couple on the end of the wire, and characterized in that said clamp means are provided with means (24–25, 128–129, 224–230) for preventing relaxation of the grip on the end of the wire to be extracted, and said seats are provided with means (21–23, 122–123, 222–223) for gripping the end of the wire, said relaxation-preventing means (24–25, 128–129, 224–230) including at least a threaded pin (24a, 124, 224) mounted at one end of one of the lever pieces for selectively locking the end of the other lever piece, said gripping means (22–23, 122–123, 222–223) having semicylindrical cavities whose diameter is approximately equal to the diameter of the wire to be extracted and whose longitudinal axis is coaxial with the longitudinal axis of the device, and having a first cylindrical end part (20a–21a, 120a–121a, 220a–221a) whose diameter is slightly greater than the diameter of the wire to be extracted and a second, generally frustoconical part joining said first part and a generally cylindrical central part of the two lever pieces thereby to enable the wire to be gripped beneath the surface of the skin.

2. Device according to claim 1, in which the clamp means are of screw type.

3. Device according to claim 2, in which said means for preventing relaxation of the grip on the end of the wire to be extracted comprise at least one screwthreaded pin (24, 124, 224) fitted with a knob and screwed into a tapped piece (25, 125, 225) carried by the end of one of said lever pieces.

4. Device according to claim 3, in which the axis of movement of said screw-type clamp means is generally parallel with one of said lever pieces (20–21).

5. Device according to claim 3, in which the axis of movement of said screw-type clamp means is generally perpendicular to the longitudinal axis of the said device.

6. Device according to claim 4, in which said hinging together of said two lever pieces is by a pivot, the end (24b) of the screwthreaded pin (24) nearest the pivot being of a generally frustoconical shape to interact with an inclined plane surface (26) formed at the end (20b) of the other lever piece in such a way as to force it outwards when said pin is screwed in.

7. Device according to claim 6, in which the hand of the thread on said pin (24) and on the tapped piece (25) is opposite to that of the thread on the wires.

8. Device according to claim 7, in which said pin (24) is provided, at the end opposite to the end (24b) having the generally frustoconical shape, with a knob having a generally polygonal cavity (40) whose longitudinal axis is coaxial with the axis of said pin, which cavity is suitable for the insertion of a polygonal socket wrench.

9. Device according to claim 8, in which said tapped piece (25) consists of a collar with a grooved surface (27) suitable for use as a knob to provide a purchase during the extraction, by unscrewing, of the wire.

10. Device according to claim 5, in which said pin (124) comprises two threaded portions (128 and 129) having threads of mutually opposite hand such that rotating said pin in one sense causes said tapped pieces and the corresponding ends of said lever pieces to move together and rotating said pin in the other sense causes said tapped pieces and the corresponding ends of the lever pieces to move apart.

11. Device according to claim 10, in which said tapped pieces (125) are formed in two cylindrical pieces (150) each inserted in one of two corresponding cylindrical cavities whose axes are generally perpendicular to those of the tapped pieces (125) located near the ends (120b, 121b) of said lever pieces (120 and 121).

12. Device according to claim 5, in which the lever piece opposite that on which said threaded pin (224) is mounted has a second knob (231) mounted on a fixed pin (230) that is generally coaxial with said pin (224).

\* \* \* \* \*